US011135403B2

(12) United States Patent
Ha et al.

(10) Patent No.: US 11,135,403 B2
(45) Date of Patent: Oct. 5, 2021

(54) SECUREMENT DEVICE AND SYSTEM

(71) Applicant: 3M INNOVATIVE PROPERTIES COMPANY, Saint Paul, MN (US)

(72) Inventors: Phong V. Ha, Hudson, WI (US); Donald G. Peterson, Shoreview, MN (US); Daniel P. Decabooter, Woodbury, MN (US); James M. Sieracki, Plymouth, MN (US)

( * ) Notice: Subject to any disclaimer, the term of this patent is extended or adjusted under 35 U.S.C. 154(b) by 0 days.

(21) Appl. No.: 17/043,059

(22) PCT Filed: Mar. 21, 2019

(86) PCT No.: PCT/IB2019/052323
§ 371 (c)(1),
(2) Date: Sep. 29, 2020

(87) PCT Pub. No.: WO2019/193445
PCT Pub. Date: Oct. 10, 2019

(65) Prior Publication Data
US 2021/0016064 A1    Jan. 21, 2021

Related U.S. Application Data

(60) Provisional application No. 62/651,754, filed on Apr. 3, 2018.

(51) Int. Cl.
*A61M 25/02* (2006.01)
(52) U.S. Cl.
CPC ....... *A61M 25/02* (2013.01); *A61M 2025/028* (2013.01); *A61M 2025/0253* (2013.01)

(58) Field of Classification Search
CPC .......... A61M 25/02; A61M 2025/0253; A61M 2025/028; A61M 2025/024; A61M 2025/0254
See application file for complete search history.

(56) References Cited

U.S. PATENT DOCUMENTS

RE24,906 E    12/1960   Ulrich
3,389,827 A    6/1968   Abere
(Continued)

FOREIGN PATENT DOCUMENTS

| AU | 2008229705 | 10/2008 |
|---|---|---|
| WO | WO 1980-001458 | 7/1980 |
| WO | 2008/151047 | 12/2008 |

OTHER PUBLICATIONS

PCT International Search Report for PCT/IB20196/052323 dated Aug. 14, 2019.

*Primary Examiner* — Theodore J Stigell
*Assistant Examiner* — John J Crawford
(74) *Attorney, Agent, or Firm* — 3M Innovative Properties Company; Trisha D. Adamson

(57) ABSTRACT

A bracket configured for use with a medical article comprising a base, a first set of posts defining a first channel, a second set of posts defining a second channel, and a support positioned in the second channel, where the first and second channels are independently dimensioned to receive at least a portion of the medical article and configured to inhibit at least lateral movement of the medical article when the medical article is coupled to the bracket. A medical article securement system for securing a medical article to the bracket and methods for coupling a medical article to the medical article securement system.

24 Claims, 4 Drawing Sheets

(56) References Cited

U.S. PATENT DOCUMENTS

| | | |
|---|---|---|
| 4,224,937 A | 9/1980 | Gordon |
| 4,250,880 A | 2/1981 | Gordon |
| 4,499,896 A | 2/1985 | Heinecke |
| 4,595,001 A | 6/1986 | Potter |
| 6,103,369 A | 8/2000 | Cast |
| 6,213,979 B1 * | 4/2001 | Bierman .............. A61M 25/02 128/DIG. 26 |
| 6,582,403 B1 | 6/2003 | Bierman |
| 6,673,046 B2 * | 1/2004 | Bierman .............. A61M 25/02 128/DIG. 6 |
| 6,770,055 B2 | 8/2004 | Bierman |
| 6,979,320 B2 | 12/2005 | Bierman |
| 7,014,627 B2 | 3/2006 | Bierman |
| 7,491,190 B2 * | 2/2009 | Bierman .............. A61M 25/02 604/174 |
| 7,947,366 B2 | 5/2011 | Ishiwatari |
| 8,100,862 B2 | 1/2012 | Bierman |
| 8,500,698 B2 | 8/2013 | Kyvik |
| 8,541,481 B2 | 9/2013 | Determan |
| 8,585,655 B2 * | 11/2013 | Bierman .............. A61M 25/02 604/180 |
| 8,608,705 B2 * | 12/2013 | Peters .............. A61M 25/02 604/174 |
| 9,457,169 B2 * | 10/2016 | Peterson .............. A61M 25/02 |
| 2002/0188255 A1 | 12/2002 | Bierman |
| 2006/0270994 A1 | 11/2006 | Bierman |
| 2009/0143741 A1 | 6/2009 | Burn |
| 2012/0041378 A1 | 2/2012 | Bierman |
| 2012/0271240 A1 * | 10/2012 | Andino .............. A61M 25/02 604/180 |
| 2013/0228510 A1 | 9/2013 | Baker, Jr. |
| 2016/0193452 A1 * | 7/2016 | Hanson .............. A61F 13/0253 602/52 |
| 2018/0154117 A1 * | 6/2018 | Roberts .............. A61M 25/02 |

\* cited by examiner

SECUREMENT DEVICE AND SYSTEM

CROSS REFERENCE TO RELATED APPLICATIONS

This application is a national stage filing under 35 U.S.C. 371 of PCT/IB2019/052323, filed Mar. 21, 2019, which claims the benefit of U.S. Provisional Application No. 62/651,754, filed Apr. 3, 2018, the disclosures of which are incorporated by reference in their entirety herein.

BACKGROUND

Various medical treatments often require the use of medical articles and tubing. In many cases the devices or tubing must be secured to a patient's body. For example, it can be necessary to introduce fluids and liquid medications directly into a blood vessel of a patient and for short term general use, a simple intravenous ("IV") line can be placed onto a patient's arm. For longer term and more specialized needs, catheters or other devices are used, such as, for example, a Foley catheter, that may be necessary for draining urine from a patient's bladder.

Healthcare providers often secure catheters and other devices or tubing to patients during hospital stays or in-home care. Securing the devices aids in proper positioning, which prevents leaks or interruptions in medication dosing, minimizes patient discomfort, and limits tangling, catching, and dislodging of connective tubing due to patient movement. In order to keep a catheter or other medical articles or tubing properly positioned for the duration of treatment, the medical article may be secured to the patient in a variety of ways.

One common way of securing a medical article or tubing to a patient is by taping the catheter or medical line to the patient's skin. However, taping can be time consuming and labor intensive. Tape can also collect contaminants and must be frequently removed and replaced. In addition, taping is not necessarily effective in securing a medical article or catheter in place, and removal of the tape may cause undesired motion of the device or catheter. Sutures have also been used to attach a catheter to a patient. With sutures, the catheter is stitched onto the patient's skin. Sutures, however, can be a source of infection, can cause pain and inflammation, and can make it more difficult to clean around the incision site. Sutures also require time and skill to place, and can cause scarring. As a result, many practitioners are moving away from securement with tapes and sutures to securement with dedicated devices that are designed to give consistent results and minimize user error.

SUMMARY

The present disclosure is generally directed to medical article securement systems and methods, and particularly, to medical article securement systems and methods that are adapted to accommodate and reliably secure a catheter systems or other medical articles including a Luer-lock style adapter. The medical article securement systems and methods of the present disclosure are generally robust, easy to use, and are designed to facilitate coupling and decoupling a medical article to and from the system, while also providing means for reliably retaining a medical article, e.g., a catheter system, for a desired treatment period.

In one aspect, provided is a bracket configured for use with a medical article, the bracket comprising a base having a longitudinal axis, a first major surface, a second major surface opposite the first major surface, a distal end, and a proximal end; a first set of posts spaced a first lateral distance apart, coupled to the first major surface of the base and extending upwardly from the base in a direction generally normal to the first major surface of the base, the first set of posts defining a first channel dimensioned to receive at least a portion of the medical article and configured to inhibit at least lateral movement of the medical article when the medical article is coupled to the bracket; a second set of posts spaced a second lateral distance apart, coupled to the base and positioned a longitudinal distance and proximal to the first set of posts and extending upwardly from the base in a direction generally normal to the first major surface of the base, the second set of posts defining a second channel dimensioned to receive at least a portion of the medical article and configured to inhibit at least lateral movement of the medical article when the medical article is coupled to the bracket; and a support positioned in the second channel, wherein the first lateral distance is greater than the second lateral distance, and wherein the first set of posts, the second set of posts, and the support are each fixed with respect to the base.

In another aspect, provided is a medical article securement system for securing a medical article, the system comprising a bracket configured to retain at least a portion of the medical article, the bracket comprising: a base having a longitudinal axis, a first major surface, a second major surface opposite the first major surface, a distal end, and a proximal end; a first set of posts spaced a first lateral distance apart, coupled to the first major surface of the base and extending upwardly from the base in a direction generally normal to the first major surface of the base, the first set of posts defining a first channel dimensioned to receive at least a portion of the medical article and configured to inhibit at least lateral movement of the medical article when the medical article is coupled to the bracket; a second set of posts spaced a second lateral distance apart, coupled to the base and positioned a longitudinal distance and proximal to the first set of posts and extending upwardly from the base in a direction generally normal to the first major surface of the base, the second set of posts defining a second channel dimensioned to receive at least a portion of the medical article and configured to inhibit at least lateral movement of the medical article when the medical article is coupled to the bracket; and a support positioned in the second channel, wherein the first lateral distance is greater than the second lateral distance, and wherein the first set of posts, the second set of posts, and the support are each fixed with respect to the base; a base dressing comprising: a first side; and a second side opposite the first side, the second side comprising a skin-contact adhesive, wherein the second major surface of the base is coupled to the first side of the base dressing; and a flap comprising: a fixed end; and a free end that is movable with respect to the bracket between a first position in which the flap is not positioned over the bracket, and a second position in which at least a portion of the flap is positioned over the bracket to further inhibit movement of the medical article relative to the bracket.

In another aspect, provided is a method for coupling a medical article to a medical article securement system, the method comprising: providing a medical article having an external surface; providing a medical article securement system of the present disclosure; moving a first portion of the medical article into the first channel; moving a second portion of the medical article into the second channel; moving the flap from the first position to the second position.

Features and advantages of the present disclosure will be further understood upon consideration of the detailed description as well as the appended claims.

Figure 1:
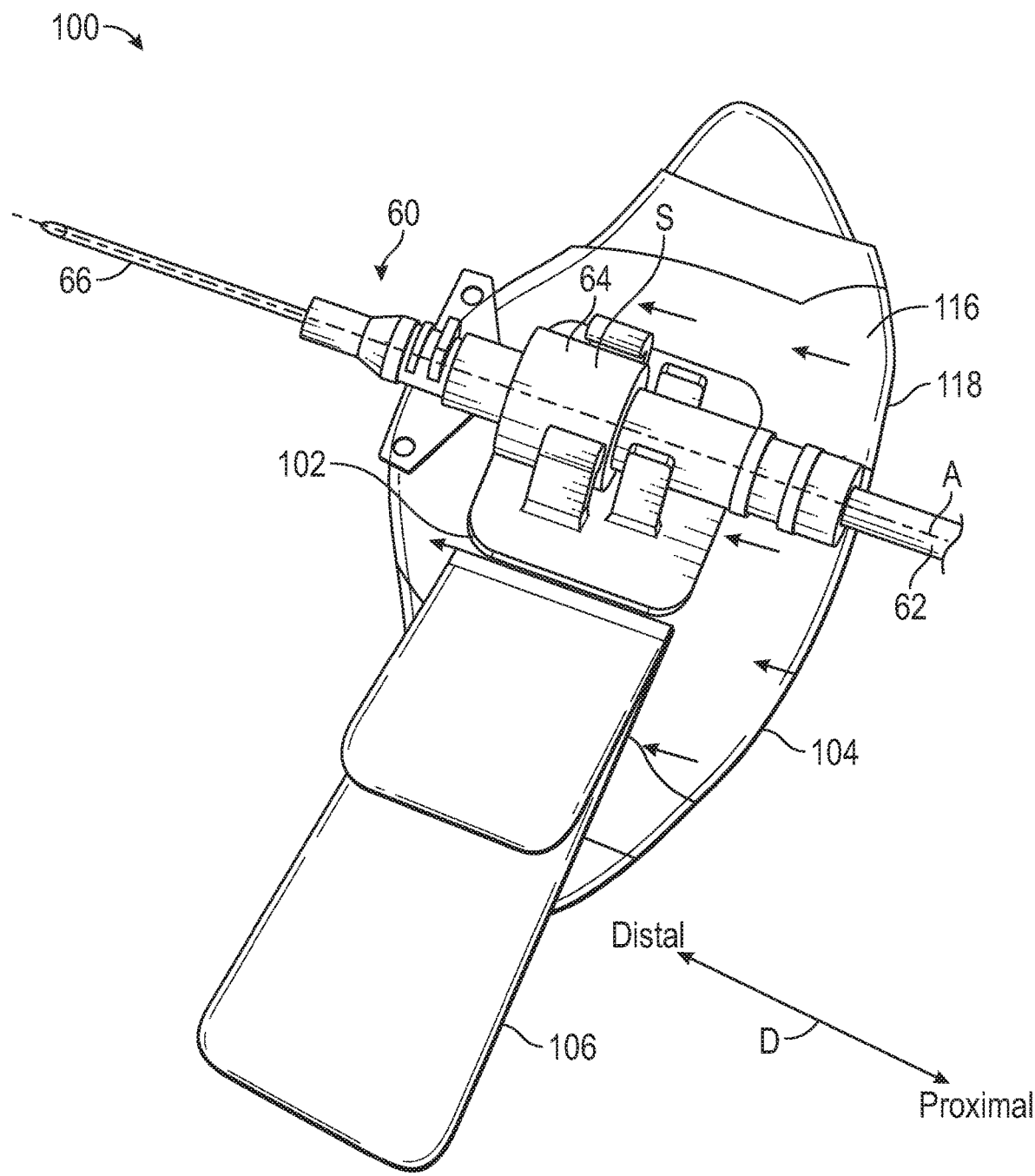
FIG. 1 is a front perspective view of a medical article securement system according to one embodiment of the present disclosure, showing a medical article coupled to a medical article securement system, the medical article securement system comprising a bracket, a flap, and a base dressing.

Repeated use of reference characters in the specification and drawings is intended to represent the same or analogous features or elements of the disclosure. It should be understood that numerous other modifications and embodiments can be devised by those skilled in the art, which fall within the scope and spirit of the principles of the disclosure. The figures may not be drawn to scale.

DETAILED DESCRIPTION

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the term "coupled" and variations thereof are used broadly and encompass both direct and indirect couplings. It is to be understood that other embodiments may be utilized, and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to medical article securement systems and methods for safely and reliably securing a medical article, such as, for example, a catheter system, upon a desired location of a patient's body. The medical article securement systems of the present disclosure accommodate and reliably secure a large variety of medical articles or class of medical articles (e.g., catheters) including a Luer-lock style adapter.

Medical article securement systems of the present disclosure provide advantages over existing securement systems that have problems such as, for example: difficulty of practitioner access to the medical device once the medical device is engaged with the securement system; the securement device is suitable only for use with catheter systems; the securement systems don't allow for inclusion of extensions to the medical article from both the distal and proximal ends of the securement system; catheter kinking once the medical article is engaged with the securement system; and patient discomfort from blood vessel irritation due to the orientation of the medical article in the securement system. To address these known problems, medical article securement systems of the present disclosure provide several solutions.

For example, to allow for easy placement of, access to, and removal of the medical article once the securement system is attached to the patient, the medical article enters and leaves the securement system from the top, i.e., from the location on the securement device furthest from the patient's skin. Other solutions provided by the presently disclosed securement systems include that they are, because of their design, not limited to use with a catheter system, but can be used for securement of many medical articles including Luer-lock style adapters, and allow for extensions from both distal and proximal ends of the securement system. Also, medical article securement systems of the present disclosure are configured to orient a medical article at a tilt angle with respect to the patient's skin, the tilt angle facilitating insertion of a portion of the medical article (e.g., a needle) into the patient, preventing kinking of the catheter, improving patient comfort, and minimizing the risk of blood vessel irritation.

Examples of medical articles that can be employed with the medical article securement system of the present disclosure include, but are not limited to, connector fittings, catheter systems (e.g., catheters, catheter hubs, catheter adaptors), fluid supply lines, line extensions (e.g., a line after an IV hub or Luer-lock style adapter), other similar articles, and combinations thereof. Examples of catheter systems can include, but are not limited to, intravenous ("IV") catheters, peripheral intravenous ("PIV") catheters, central venous catheters ("CVCs"), peripherally inserted central catheters ("PICCs"), arterial catheters, and dialysis catheters.

The terms "longitudinal" and "axial" are used to refer to a direction or axis that is generally parallel to the direction in which the medical article extends and generally parallel to the overall direction of fluid flow, e.g., along a catheter line.

The term "lateral" is used to refer to a direction or axis that is generally perpendicular to the longitudinal axis or direction and is used to represent side-to-side motion of a medical article.

The terms "vertical" and "normal" are used to refer to a direction or axis that is normal to both the longitudinal and lateral directions or axes, as well as to the surface of a patient's skin when the medical article securement system is coupled to the patient's skin, and is used to represent the direction of motion toward and away from the skin surface.

The term "proximal" and "distal" are used to represent axial directions, relative to a medical practitioner operating or holding the medical article. That is, the term "distal" is used to refer to the direction away from the medical practitioner (and toward an insertion site on the patient and inside the patient's body), and the term "proximal" is used to refer to the direction toward the medical practitioner (and toward the outside of the patient's body, away from the insertion site). For example, the distal end of a catheter is inserted into the patient, while the proximal end extends exterior of the patient toward the medical practitioner. The distal end of the medical article securement system refers to the end of the system that is configured to be oriented toward the distal end of the medical article to which it will be coupled, and the proximal end of the medical article securement system refers to the end of the system that is configured to be oriented toward the proximal end of the medical article. As a result, in the case of catheter systems, the distal end of the medical article securement system will be oriented toward the insertion site on the patient's body, and the proximal end of the of the medical article securement system will be oriented away from the insertion site on the patient's body.

Figure 2:
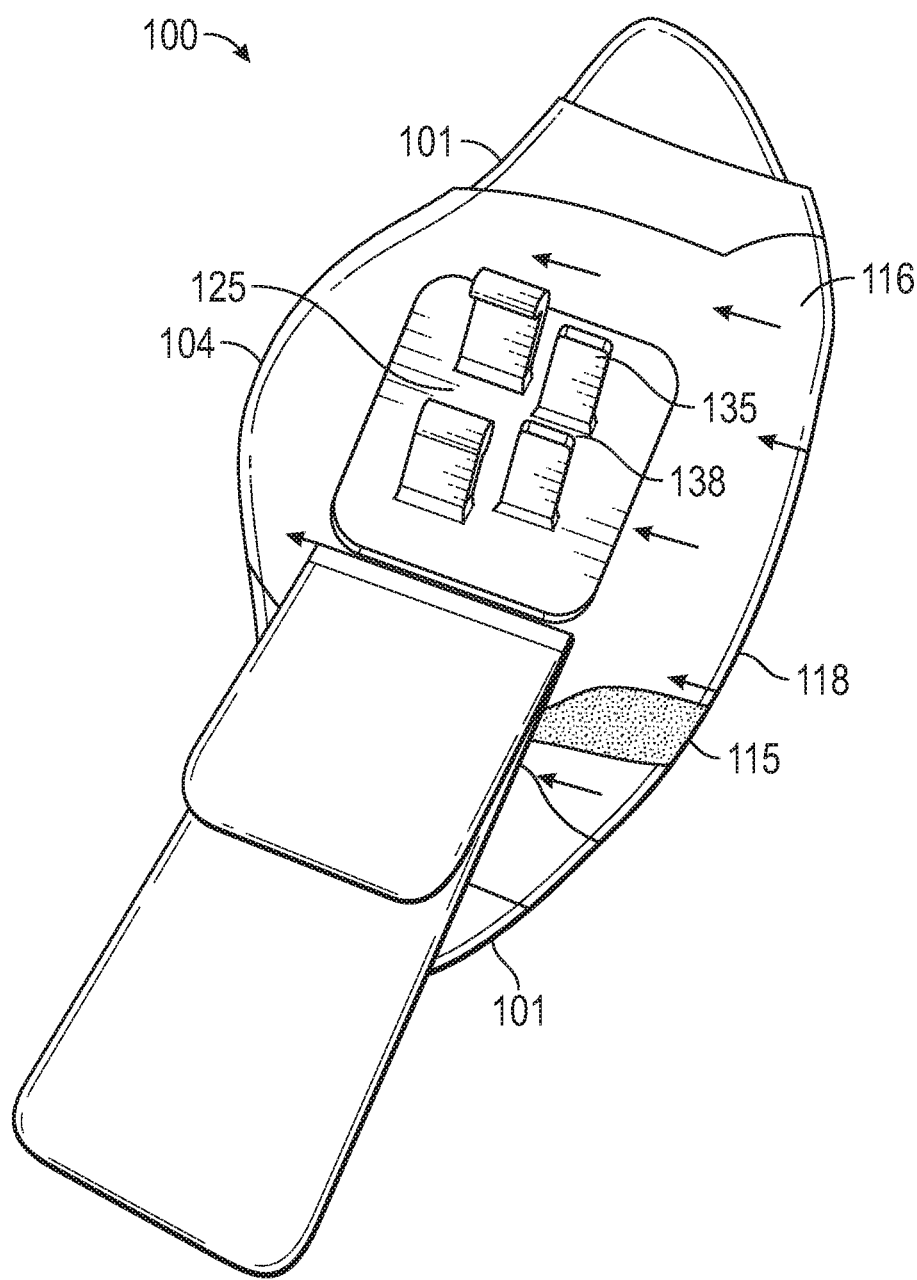
FIG. 2 is a front perspective view of the medical article securement system of FIG. 1, shown without the medical article, prior to coupling to a patient.
Figure 3:
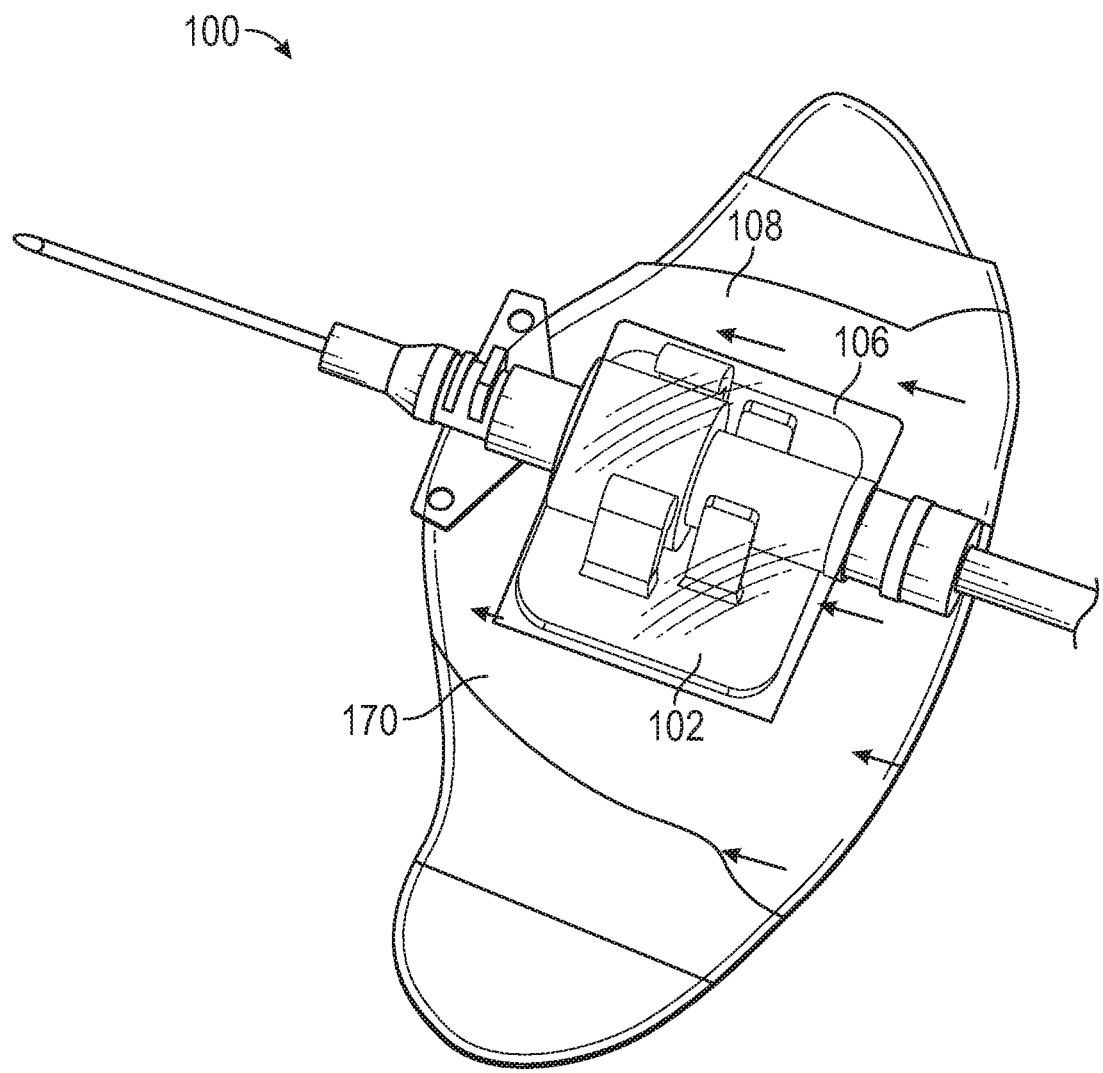
FIG. 3 is a front perspective view of the medical article securement system of FIG. 1, shown with the flap extending laterally over the bracket and medical article.
Figure 4:
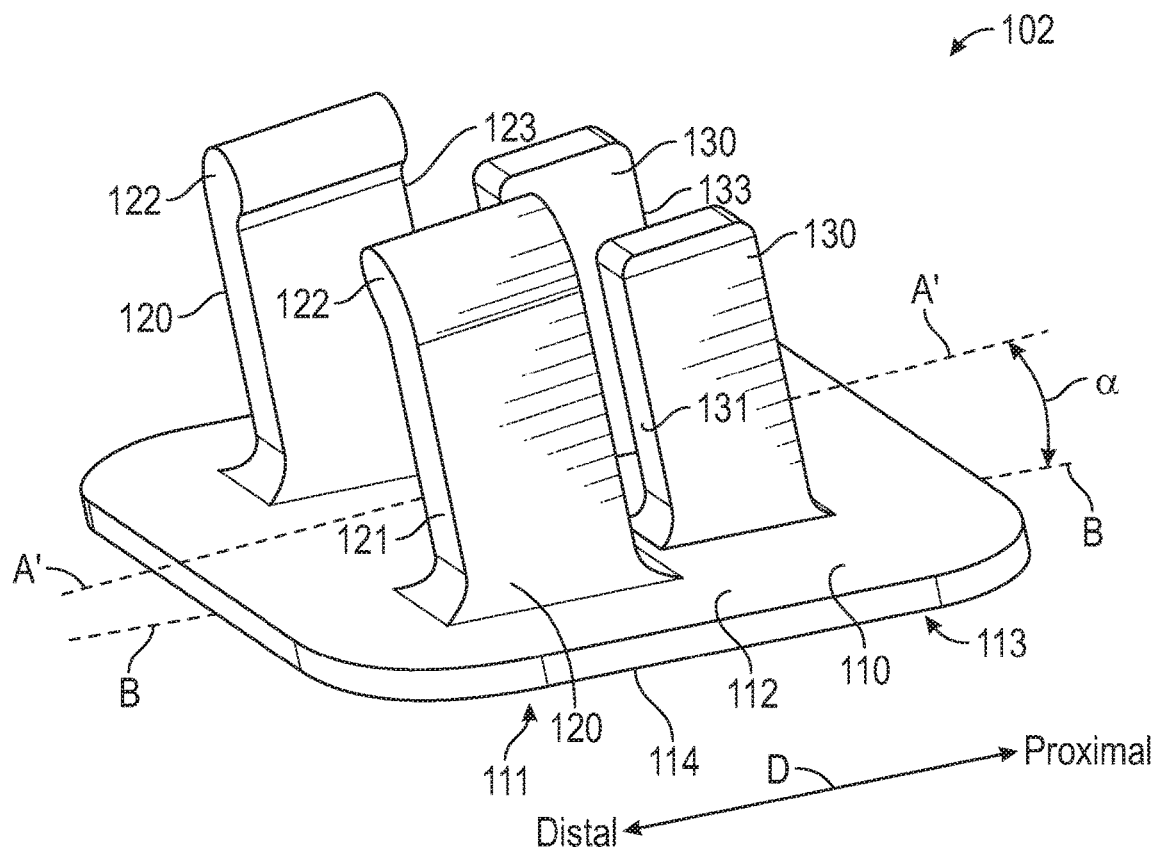
FIG. 4 is a side perspective view of another embodiment of the bracket of the medical article securement system of FIGS. 1-3.

FIGS. 1-4 illustrate a medical article securement system 100 according to one aspect of the present disclosure. FIG. 1 illustrates an exemplary medical article 60 coupled to the securement system 100. By way of example only, the medical article 60 is illustrated as being a catheter system having one input catheter (or tube or line) 62, a Luer-lock style adapter 64, and one output catheter (or tube or line or needle) 66. FIG. 2 shows the securement system 100 prior to coupling the securement system 100 to the medical article 60. FIG. 3 illustrates an exemplary medical article 60 coupled to the securement system 100 and flap 106 extending laterally over the bracket 102 and medical article 60. FIG. 4 shows the bracket 102 of the securement system 100. As shown, the medical article 60 can have a longitudinal axis A that extends along and defines a longitudinal direction D.

As shown in FIGS. 1-3, the securement system 100 can include a bracket (or "retaining bracket" or "retainer") 102, a base dressing 104, and a flap 106. The bracket 102 and other components of the securement system 100 can be coupled to the base dressing 104, and the base dressing 104 can be adhered to the patient's skin. The flap 106, can be used in addition to bracket elements to further secure the medical article 60 to the securement system 100.

Referring to FIG. 4, the bracket 102 can include a base (or "platform") 110. The base 110 (or the bracket 102 or the system 100) can include a longitudinal axis A' that is oriented along or parallel to the longitudinal axis A of the medical article 60 when the medical article 60 is coupled to the bracket 102. That is, when the medical article 60 is coupled to the bracket 102, the longitudinal axis A of the medical article 60 can be generally aligned with (which can include directly overlapping or just parallel to) the longitudinal axis A' of the base 110. The longitudinal axis A' of the base 110 (or the bracket 102) also extends along or defines the longitudinal direction D.

The base 110 can include a first major surface 112 (e.g., an upper surface) configured to face away from the patient's skin and to receive at least a portion of the medical article 60, the first major surface 112 defining a first plane including longitudinal axis A'. The base 110 can further include a second major surface 114 (e.g., a bottom surface) opposite the first major surface 112 that is configured to face the patient's skin and to be securely coupled (e.g., adhered) to the base dressing 104, the second major surface 114 defining a second plane including longitudinal axis B, as shown in FIG. 4. In some embodiments the first major surface 112 may be generally parallel to the second major surface 114, such that an angle α between the first major surface 112 and the second major surface 114 is 0°.

The base 110 (or the bracket 102) can further include a distal end (or first longitudinal end) 111 and a proximal end (or second longitudinal end) 113, such that, for example, the distal end 111 is configured to be positioned away from a medical practitioner operating or holding the medical article 60, and the proximal end 113 is configured to be positioned toward the medical practitioner. The longitudinal axes A' and B can extend in the longitudinal direction (e.g., as defined by the medical article 60) between the distal end 111 and the proximal end 113. In some embodiments and as shown in FIG. 4, the first major surface 112 and the second major surface 114 may form an acute angle α less than 30°, less than 25°, or less than 20° (e.g., 14°, such that the base 110 is thicker at the proximal end 113 and thinner at the distal end 111. Having a bracket 102 that is thicker at the proximal end 113 and thinner at the distal end 111, as described above, may desirably allow a medical article 60 positioned in the bracket 102 to be tilted at an angle toward a location on a patient's skin where a portion of the medical article 60 is inserted. This tilt angle may be beneficial by facilitating insertion of a portion of the medical article 60 into the patient, preventing kinking of the catheter, and by placing the medical article 60 in an orientation that may improve patient comfort and minimize the risk of blood vessel irritation.

A base 110 of the present disclosure can be constructed of either rigid or flexible materials. The base 110 can have any suitable shape or footprint. In some embodiments, the base 110 may have a rectangular shape.

Referring to FIGS. 1-3, the base dressing 104 includes a first side 116 configured to face away from the patient's skin, and a second side 118 opposite the first side 116 that comprises a skin-contact adhesive 115 (see FIG. 2) for adhering to the skin. The second major surface 114 is configured to be coupled to the first side 116 of the base dressing 104. Although only a single shape of the base dressing 104 is illustrated, it should be understood that the base dressing 104 can take on a variety of shapes and sizes, depending on the shapes and configurations of the other elements of the system 100 and the medical article 60 to be coupled to the system 100. In some embodiments, the base dressing 104 comprises a laminated structure comprising one or more of a fabric, a woven fibrous web, a nonwoven fibrous web, a knit, a polymeric film, or combinations thereof.

The skin-contact adhesive 115 is generally a pressure-sensitive adhesive, and particularly is a pressure-sensitive adhesive that is capable of securely but releasably adhering or bonding to skin (e.g., mammalian skin). The skin-contact adhesive 115 may be applied to the second side 118 of the base dressing 104 in a continuous or discontinuous layer. In some embodiments, the skin-contact adhesive 115 may be applied to the second side 118 of the base dressing 104 in a pattern, such as, for example, dots, lines, a grid, or a lattice. Examples of patterns for skin-contact adhesives 115 that can be employed with the systems of the present disclosure include, but are not limited to, the adhesive patterns described in U.S. Pat. No. 4,595,001 (Potter et al.) and U.S. Pat. No. 7,947,366 (Ishiwatari et al.) which are incorporated herein by reference in their entireties.

The skin-contact adhesive 115 is also generally safe and non-toxic. Skin-contact adhesive 115 layers will generally be selected according to the desired end use of the base dressing 104. In some embodiments, the base dressing 104 can include more than one skin-contact adhesive 115. Where the base dressing 104 comprises more than one skin-contact adhesive layer 115, each skin-contact adhesive layer 115 may be selected independently of each other with regard to material and thickness used. Examples of suitable adhesives include acrylates, silicones, polyisobutylenes, synthetic rubber, natural rubber, and copolymers and mixtures thereof.

Acrylates and silicones can be preferred skin-contact adhesives 115. In general, the skin-contact adhesive 115 should cause little or no irritation or sensitization of the skin during the intended wear period. Examples of skin-contact adhesives 115 that can be employed with the systems of the present disclosure include, but are not limited to, the adhesives described in U.S. Pat. Nos. RE 24,906; 3,389,827; 6,103,369; and 4,499,896, which are incorporated herein by reference in their entireties. In addition, silicone adhesives such as those described in U.S. Pat. No. 8,541,481, (Determan, et al.) which is incorporated herein by reference in its entirety, can also be employed.

In some embodiments, e.g., in embodiments employing silicone adhesives, the base dressing 104 and the skin-contact adhesive 115 can be perforated to provide openings from the first side 116 of the base dressing 104 all the way through the second side 118 and the skin-contact adhesive 115, which can enhance permeability of the base dressing 104 and can minimize moisture build-up at the skin surface underlying the base dressing 104.

As shown in FIGS. 1-3, in some embodiments, the securement system 100 can further include one or more release liners 101 that can provide a release layer or surface to the skin-contact adhesive 115 on the second side 118 of the base dressing 104 prior to use. By way of example only, as shown in FIG. 2, the securement system 100 includes two butterfly-configured release liners 101, such that one portion (e.g., one lateral half) of the base dressing 104 can be applied at a time to the patient's skin to facilitate adhering the securement system 100 to the skin in a desired orientation without any crinkling or folding of the base dressing 104 before it is ready to be applied. The release liners 101 are illustrated as being symmetrical, however, this need not be the case, depending on the shape and configuration of the base dressing 104.

Examples of liners suitable for use with systems of the present disclosure can include, but are not limited to, kraft papers, polyethylene, polypropylene, polyester, or combinations thereof. Such liners can be coated with release agents, such as fluorochemicals, silicones, or other suitable low surface energy materials. Other adhesives and release liner 101 combinations known to those of ordinary skill in the art can be employed in the systems of the present disclosure.

The bracket 102 (e.g., the second major surface 114 of the base 110) can be coupled to the base dressing 104 using a variety of coupling means including, but not limited to, one or more of adhesives, cohesives, magnets, welding (e.g., sonic [e.g., ultrasonic] welding), a thermal bonding or heat sealing technique (e.g., heat and/or pressure applied to one or both of the components to be coupled), other suitable coupling means, or combinations thereof.

The bracket 102 further includes a distal set of vertical posts 120 coupled to the base 110 that extend upwardly from the base 110, away from the first major surface 112 of the base 110 and the patient's skin, in a direction generally normal to the first major surface 112. In some embodiments distal posts 120 may extend, at most, 7 mm to 11 mm (e.g., 9 mm) from the first major surface 112 of the base 110. In some embodiments, the distal posts 120 may be angled distally from 1° to 30°, from 5° to 18°, from 5° to 10°, or from 6° to 8°, e.g., 7°, from a direction generally normal to the first major surface 112 of the base 110.

The distal posts 120 can be spaced a lateral distance apart to define a first channel 125 therebetween that is dimensioned to receive at least a portion of the medical article 60. In some embodiments, the first channel 125 is dimensioned to receive a Luer-lock style adapter 64. The Luer-lock style adapter is a standardized connector within the medical community. The specifications for a Luer-lock style adapter can be found in ISO 80369-7 standards. In some embodiments, the Luer-lock style adapter 64 may include a male Luer protrusion adapted to mate with a female Luer fitting of output catheter 66 and a rotatable collar adapted to reversibly secure the male Luer protrusion to the female Luer fitting. In some embodiments, the lateral distance between the distal posts 120 may decrease as the distal posts 120 extend upwardly from the base 110, away from the first major surface 112 of the base 110. In some embodiments, the lateral distance between the distal posts 120 may increase as the distal posts 120 extend upwardly from the base 110, away from the first major surface 112 of the base 110. In some embodiments, the lateral distance between the distal posts 120 may remain generally constant as the distal posts 120 extend upwardly from the base 110, away from the first major surface 112 of the base 110.

The bracket 102 further includes a proximal set of vertical posts 130 coupled to the base 110 that extend upwardly from the base 110, away from the first major surface 112 of the base 110 and the patient's skin, in a direction generally normal to the first major surface 112. In some embodiments distal posts 120 may extend, at most, 5 mm to 10 mm 110 (e.g., 6 mm, 7 mm, 8 mm, 9 mm) from the first major surface 112 of the base 110. In some embodiments, the proximal posts 130 may be tilted distally from 1° to 30°, from 5° to 18°, from 5° to 10°, or from 6° to 8°, e.g., 7°, from a direction generally normal to the first major surface 112 of the base. In some embodiments, the distal posts 120 and the proximal posts may be tilted distally at the same angle, for example, from 1° to 30°, from 5° to 18°, from 5° to 10°, or from 6° to 8°, e.g., 7°, from a direction generally normal to the first major surface 112 of the base 110. In some embodiments, the distal set of vertical posts 120 may extend further from the first major surface 112 of the base 110 than the proximal set of vertical posts 130.

Embodiments of brackets 102 and securement systems 100 of the present disclosure where the distal set of vertical posts 120 and the proximal set of vertical posts 130 of the bracket 102 are tilted distally from a direction generally normal to the first major surface 112 of the base 110 may provide performance advantages over brackets 102 including a distal set of vertical posts 120 and a proximal set of vertical posts 130 that are not tilted distally from a direction generally normal to the first major surface 112 of the base 110. Such advantages may include, for example, improved positioning of the medical article 60 along the longitudinal axis A during use due to increased contact between portions of the securement system 100 (e.g., surfaces of distal ends 131 of the proximal set of vertical posts 130 of the bracket 102, retaining features 122 of the distal set of vertical posts 120 of the bracket 102) and the medical article 60. Improved positioning of the medical article 60 may have many benefits, including, for example, less opportunity for undesirable lateral, vertical, and/or longitudinal movement of the secured medical article, and reduction or elimination of tubing kinking, particularly when the medical article is a catheter system.

The proximal posts 130 can be spaced a lateral distance apart to define a second channel 135 therebetween that is dimensioned to receive at least a portion of the medical article 60. As shown in FIGS. 1-4, the lateral distance between the proximal posts 130 is less than the lateral distance between the distal posts 120, i.e., the first channel 125 is wider than the second channel 135, such that the second channel 135 is too narrow to receive a Luer-lock style adapter 64. In some embodiments, the lateral distance between the proximal posts 130 may decrease as the proximal posts 130 extend upwardly from the base 110, away from the first major surface 112 of the base 110. In some embodiments, the lateral distance between the proximal posts 130 may increase as the proximal posts 130 extend upwardly from the base 110, away from the first major surface 112 of the base 110. In some embodiments, the lateral distance between the proximal posts 130 may remain generally constant as the proximal posts 130 extend upwardly from the base 110, away from the first major surface 112 of the base 110.

The proximal set of vertical posts 130 is positioned a longitudinal distance from the distal set of vertical posts 120. In some embodiments, the longitudinal distance between the proximal set of vertical posts 130 and the distal set of vertical posts 120 can be 1 mm to 12 mm, 1 mm to 8 mm, or 1 mm to 4 mm (e.g., 2 mm). In some embodiments, the surfaces of distal ends 131 of the proximal set of vertical posts 130 and surfaces of distal ends 121 of the distal set of vertical posts 120 overlap with each other less than 50%, less than 40%, less than 30%, less than 20%, or less than 10% when the distal end 121 surfaces are projected onto a reference plane normal to the first major surface 112. In some embodiments, the surfaces of distal ends 131 of the proximal set of vertical posts 130 and surfaces of distal ends 121 of distal set of vertical posts 120 do not overlap with each other when the distal end 121 surfaces are projected onto a reference plane normal to the first major surface 112.

As shown, the first channel 125 and the second channel 135 can be oriented generally along (i.e., parallel to or overlapping) the longitudinal axes A and A' of the medical article 60 and the base 110, respectively, such that each channel 125, 135 can be referred to as a "longitudinal channel" In some embodiments, the first channel 125 and the second channel 135 can be generally aligned, for example, such that their respective lateral centers are aligned with each other, and optionally, further aligned with the longitudinal axis A' of the base 110.

Each post 120, 130 can include a distal end 121,131 positioned toward the distal end 111 of the base 110 and a proximal end 123, 133 positioned toward the proximal end 113 of the base 110. The distal end 131 of the proximal posts 130 (as shown in FIG. 4) can be configured to abut a surface S on the medical article 60 to inhibit at least longitudinal movement (e.g., proximally) of the medical article 60 when the medical article 60 is coupled to the bracket 102. Specifically, the proximal posts 130 can be configured to abut, and provide a (longitudinal) stop for an external surface S of the medical article 60. By way of example only, the external surface S is illustrated as being a proximal surface or end of the Luer-lock type adaptor 64. In such embodiments, the proximal posts 130 can function as a longitudinal proximal stop and can be configured to inhibit proximal movement of the medical article 60 to inhibit the medical article 60 from moving away from the patient (e.g., to inhibit the output catheter 66 from being pulled out of the insertion site of the patient after it has been properly inserted). In some embodiments, the external surface S may be a vertical surface of the medical article in that the surface S extends substantially normal with respect to the patient's skin and the first major surface 112 of the base 110 of the bracket 102. In some embodiments, the surface S on the medical article 60 may be a rotatable surface, such as, for example, a rotatable collar on Luer-lock style adapter.

By being configured to abut an external surface S of the medical article 60, each of the proximal posts 130 can facilitate coupling and decoupling of the medical article to the bracket 102 without requiring that any portion of the bracket 102 be forced through any portion of the medical article 60 (e.g., suture holes of a catheter hub or wing) or snapped onto the medical article 60. As a result, no portion of the medical article 60 and/or the bracket 102 needs to be so firmly pressed toward the patient's skin or the bracket 102 during application, or firmly pulled away from the patient's skin during removal, which can cause disruption of the insertion site or undesirable movement of the medical article 60 relative to the patient's skin.

Typically, the posts 120,130 are not located tightly adjacent the distal end 111 or the proximal end 113 of the base 110 to allow a distal portion and a proximal portion of the first major surface 112 of the base 110 to be exposed to support at least a portion of the medical article 60.

As shown for the posts 120, 130, the term "post" is generally used to refer to a structure that is open on all sides, such that the posts 120, 130 are not coupled to other elements of the bracket 102 on their sides. Rather, portions of the medical article 60 can be positioned on all sides of each post 120, 130 if necessary.

In some embodiments, and as shown in FIG. 4, the distal posts 120 can include a retaining feature 122, such as a protrusion, a nub, a rib, or the like, which can at least partially inhibit the medical article 60 from being removed from the first channel 125 after it has been positioned in the first channel 125. That is, the retaining feature 122 can inhibit movement of the medical article 60 in a vertical direction away from the base 110.

Figure 5:
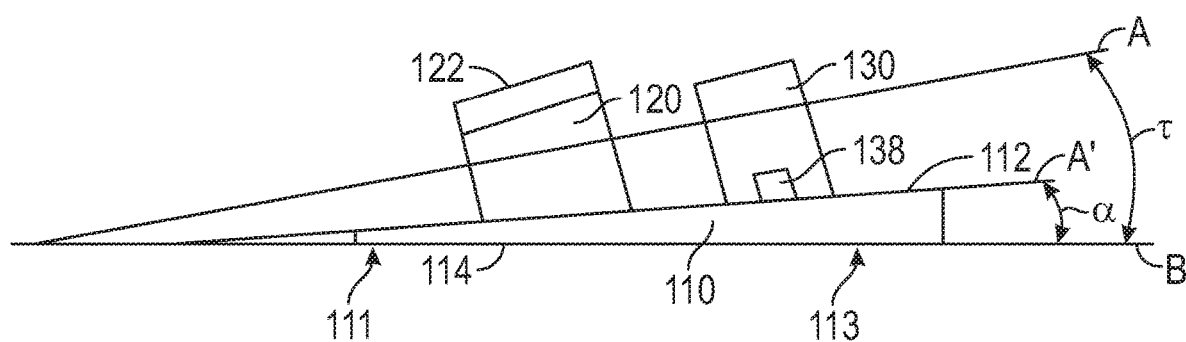
FIG. 5 is a side section view of a bracket according to one embodiment of the present disclosure.

The bracket 102 further includes a support 138 positioned in at least the second channel 135. The support 138 is configured to hold up at least a portion of the medical article 60 in the second channel 135 such that the longitudinal axis A of the medical article 60 slopes downward from the support 138 toward the distal end 111 of the base 110. Desirably the medical article 60 slopes downward from the support 138 toward the distal end 111 of the base 110 at an angle of from 1° to 30° (e.g., 15°) relative to the second major surface 114. In some embodiments, the support 138 may be coupled to the base 110 and extend upwardly from the base 110, away from the first major surface 112 of the base 110 and the patient's skin, in a direction generally normal to the first major surface 112. In some embodiments, the support 138 may extend 1 mm to 4 mm (e.g., 2 mm) from the first major surface 112 of the base 110. The support 138 may have any suitable shape, such as, for example, square, rectangular, trapezoidal, cylindrical, pyramidal, or conical. In some embodiments, the support 138 may be coupled to one or both proximal posts 130 such as, for example, a bar extending across the lateral distance between the proximal posts 130. In some embodiments, the support 138 is positioned in the second channel 135 but not in the first channel 125. In some embodiments, and as shown in FIG. 5, the support 138 is a component of a bracket 102 having a base 110 that is thicker at the proximal end 113 and thinner at the distal end 111. In some embodiments, the support is a component of a bracket 102 having a base 110 that has the same thickness at the proximal end 113 and the distal end 111.

As a result of the cooperation of at least the posts 120, 130, the support 138, the base, 110, and the flap 106, the medical article 60 is inhibited from movement in the lateral, longitudinal, and vertical directions (e.g., relative to the bracket 102) when coupled to the system 100.

As discussed above with respect to the bracket 102 base 110, the support 138 may facilitate the positioning of a medical article 60 in the bracket 102 so that the medical article 60 may be tilted at an angle toward a location on a patient's skin where a portion of the medical article 60 is inserted. As shown in FIG. 5, this medical article tilt angle τ is defined by the angle between a third plane including longitudinal axis A of the medical article 60, the third plane being coplanar with the second plane, i.e., the plane including the second major surface 114, when τ is 0°. The medical article tilt angle τ may provide benefits when using the securement device 100 with a patient by facilitating insertion of a portion of the medical article 60 into the patient and by securing the medical article 60 in an orientation that makes it less likely that damage to the patient's blood vessel will occur. Preferably, the medical article tilt angle τ is 5° to 30°, 8° to 25°, or 10° to 20° (e.g., 15°). In some preferred embodiments, the combined effects of certain bracket 102 features, i.e., a base 110 that is thicker at the proximal end 113 and thinner at the distal end 111 and a support 138, result in the medical article 60 tilting at an angle τ toward a location on a patient's skin where a portion of the medical article 60 is inserted.

As further shown in FIGS. 1-4, the posts 120, 130 and support 138 can be fixed with respect to the base 110 and to each other, such that, in some embodiments, the bracket 102 includes no moving parts, which can enhance manufacturability of the bracket 102 and can also reduce the complexity of the bracket 102, while also minimizing the number of elements that can fail or fracture during use. In the embodiment of FIGS. 1-4, the posts 120, 130 and the support 138 are integrally formed with the base 110; however, this need not be the case. In some embodiments, the posts 120, 130 and the support 138 can be coupled to the base 110 in order to be fixed with respect to the base 110. In some embodiments, the posts 120, 130 and the support 138 are directly coupled to the base 110 such that no intervening elements or structures are positioned or coupled between the posts 120, 130 and the base 110 or between the support 138 and the base 110, and in some embodiments, the posts 120, 130 and the support 138 may be indirectly coupled to the base 110 by additional structures or elements.

The bracket 102, e.g., the base 110, the posts 120,130, the support 138, may be formed integrally from a unitary material to form a unitary piece by methods known in the art, such as, for example, injection molding, extrusion molding, 3D printing. In some embodiments, elements of the bracket 102 are independently formed from differing materials. In some embodiments, elements of the securement device 100 are independently formed from the same material. The robustness of the materials used to make the securement device 100 of the present disclosure can offer facile, reliable, and secure coupling of a medical article 60 to bracket 102.

Brackets 102 of the present disclosure can be constructed of any suitable material that allows both appropriate flexibility and rigidity. In some embodiments, brackets of the present disclosure may be constructed of polymeric or elastomeric materials. In some embodiments, the brackets of the present disclosure may be constructed of metals, plastics, or composites. Exemplary materials include ABS plastic, polypropylene, polycarbonate, polyethylene, polyvinylchloride, acrylonitrile butadiene styrene, nylon, olefins, acrylics, polyesters, silicones, thermoplastic urethane, thermoplastic elastomers, and the like. In some embodiments, the bracket 102 may comprise polycarbonate.

Some embodiments of the systems of the present disclosure can include a flap, such as the flap 106 shown in FIGS. 1-3. The systems of the present disclosure can include a flap 106 and a bracket 102, as disclosed above, comprising a base 110, posts 120, 130, and support 138. In some embodiments, when the flap 106 is extended laterally over the bracket 102 and medical article 60, the flap 106 may contact at least one of the sets of posts 120, 130 and/or a portion of the Luer-lock style connector, thereby providing security to inhibit lateral, longitudinal, rotational, and/or vertical movement of the medical article (e.g., the medical article 60). In some embodiments, when the flap 106 is extended laterally over the bracket 102 and medical article 60, the flap 106 may contact only one of the sets of posts 120, 130 and/or a portion of the Luer-lock style connector, thereby providing security to inhibit lateral, longitudinal, rotational, and/or vertical movement of the medical article (e.g., the medical article 60). In some embodiments, when the flap 106 is extended laterally over the bracket 102 and medical article 60, the flap 106 may contact a portion of the Luer-lock style connector but not contact either of the sets of posts 120, 130, thereby providing security to inhibit lateral, longitudinal, rotational, and/or vertical movement of the medical article (e.g., the medical article 60).

The flap 106 of the present disclosure can be flexible, particularly, relative to the bracket 102 of the present disclosure, and the bracket 102 can be relatively rigid, relative to the flap 106. The flap 106 can therefore provide a more pliable and compliant element to the systems of the present disclosure to complement and supplement the structural rigidity and integrity of the bracket 102. The robustness of the bracket 102 of present disclosure can offer facile, reliable, and secure coupling and decoupling of a medical article to the bracket, and the flap 106 of the present disclosure can provide additional security. The flap 106 of the present disclosure can also provide a certain level of flexibility depending on the specific medical article that is being coupled to the system 100, because the flap 106 can be sized and configured to accommodate a variety of medical article configurations and sizes. For example, the flap 106 can be long enough to accommodate a variety of medical articles, and can simply be pulled further over the bracket 102 and medical article in cases of smaller medical articles. The flexibility of the flap 106 is generally sufficient to prevent the flap from breaking (e.g., adjacent its hinge), while still being rigid enough to provide structural integrity and to inhibit movement of the medical article when the medical article is coupled to the system.

The flap 106 of the present disclosure can be formed of a variety of materials, including, but not limited to, at least one of a fabric, a woven fibrous web, a nonwoven fibrous web, a knit, a polymeric film, an elastomer, combinations thereof, or a laminate structure comprising any of the above. In some embodiments, the flap 106 can include a backing (e.g., formed of any of the above-listed materials) and an adhesive (e.g., where the adhesive serves as securing means for the flap). In some embodiments, the flap 106 can be formed from a medical tape, such as medical tapes available under the tradenames DURAPORE and TRANSPORE from 3M Company, St. Paul, Minn. The flap 106 of the present disclosure (i.e., the backing of the flap) generally needs to be sufficiently flexible to conform to a portion of the medical article 60 and sufficiently rigid to resist deformation when axial, vertical and/or lateral forces are applied. In some embodiments, the flap 106 (i.e., the backing of the flap) can have a thickness ranging from about 1 mil (0.02 mm) to about 6 mil (0.15 mm). The securing means of the flap 106 should generally have sufficient adhesion to securely attach to the medical article 60 while also being able to be removed cleanly (i.e., with little to no residue, if the securing means comprises an adhesive).

Additional details regarding flap 106 of the present disclosure can be found in U.S. Pat. No. 9,457,169 (Peterson et al.), which is incorporated herein by reference in its entirety.

As shown in FIGS. 1-3, the flap 106 can include a first fixed end 170 and a second free end 172 that is movable with respect to the first fixed end 170, the bracket 102 and the medical article 60 between a first position $P_1$ (see FIGS. 1 and 2) in which the flap 106 is not positioned over the medical article 60 and/or the bracket 102 and a second position $P_2$ (see FIG. 3) in which at least a portion of the flap 106 is positioned over (i.e., in overlapping relationship with) the bracket 102 (and the medical article 60 when the medical article 60 is coupled to the system 100). In some embodiments, the flap 106 can extend across the longitudinal axis A' of the base 110 when the flap 106 is in the second position $P_2$.

The flap 106 can also be positioned over the medical article 60 when in the second position $P_2$ when the medical article 60 is coupled to the bracket 102. In the second position $P_2$, the flap 106 can further inhibit movement of the medical article 60 relative to the bracket 102. In addition, the flap 106 is different from a separately provided piece of tape or other strip or fastener, because the flap 106 is provided by the system 100, and particularly is provided in a specific configuration and arrangement relative to the other components of the system 100 to provide facile and effective use of the flap 106. That is, the first fixed end 170 of the flap 106 can be coupled to the bracket 102 when the second free end 172 of the flap 106 is in the first position $P_1$ and the second position $P_2$, e.g., the flap 106 is somehow coupled to the system 100, and particularly, the bracket 102, even before the flap 106 is used.

In some embodiments, the flap 106 can be directly coupled to the bracket 102 (e.g., to the second major surface 114 of the bracket), and in some embodiments, the flap 106 can be indirectly coupled to the bracket 102, such as, for example, coupled to or provided by another component of the system 100 that is coupled to the bracket 102, such as the base dressing 104, as shown in FIGS. 1-3.

In the embodiment illustrated in FIGS. 1-3, the flap 106 is oriented substantially perpendicularly with respect to the longitudinal axis A' of the base 110; however, it should be understood that in some embodiments, the flap 106 can extend at an oblique angle with respect to the longitudinal axis A', such that the flap 106 still includes a lateral component and crosses over the bracket 102 but not at a 90-degree angle. That is, in some embodiments, the flap 106 can be oriented at a non-zero and non-right angle with respect to the longitudinal axis A' of the base 110 of the bracket 102, at least when the free end 172 of the flap 106 is in the second position $P_2$.

As shown in FIG. 2, in some embodiments, the fixed end 170 of the flap 106 can include a hinge (e.g., a living hinge) 174 about which the free end 172 of the flap 106 can pivot to move between the first position $P_1$ and the second position $P_2$. Such a hinge 174 can be formed in the flap material itself, or in another component of the system 100 to which the flap 106 is coupled, such as the base dressing 104.

As shown in FIGS. 1-3, the bracket 102 and the flap 106 can be coupled to the first side 116 of the base dressing 104. In some embodiments, the fixed end 170 of the flap 106 can be coupled (e.g., sandwiched) between the bracket 102 and the base dressing 104, i.e., between the second major surface 114 of the bracket 102 and the first side 116 of the base dressing 104.

The flap 106 can be coupled to portions of the bracket 102 or the base dressing 104, or between the bracket 102 and the base dressing 104 using a variety of coupling means including, but not limited to, one or more of adhesives, cohesives, magnets, welding (e.g., sonic (e.g., ultrasonic) welding), any thermal bonding or heat sealing technique (e.g., heat and/or pressure applied to one or both of the components to be coupled), other suitable coupling means, or combinations thereof.

At least the free end 172 of the flap 102, and sometimes an entire side of the flap 106, can include securing means. Such securing means can include, but are not limited to, one or more of an adhesive, a cohesive, a hook and loop fastener that mates with a pad located on another element of the system 100 (e.g., the base dressing 104 on an opposite side of the bracket 102 from the fixed end 170 of the flap 106), other suitable securing or fastening means, or combinations thereof.

In some embodiments, and as shown in FIGS. 1-3, the securement system 100 may further include indicia 108, such as arrows, to indicate how the system 100 should be oriented relative to another device, structure, or portion of a patient's body. Base dressings of the present disclosure can also include such directional cues.

Method of Use

A securement system 100 of the present disclosure can be used to reliably secure a catheter system or other medical articles including a Luer-lock style adapter to a patient. The medical article 60 comprising an external surface S can be coupled to the system 100 by first orienting the longitudinal axis A of the medical article 60 along longitudinal axis A' of the securement system 100. The method can then include moving a first portion of the medical article 60 into the first channel 125 such that the Luer-lock style adapter 64 of the medical article 60 is positioned below a retaining feature 122, if present, and the external surface S of the Luer-lock style adapter 64 abuts the distal ends 131 of the posts 130. The method further includes moving a second portion of the medical article 60 into the second channel 135 such that it rests on support 138.

Once the medical article 60 is positioned in the bracket 102, the flap 106 can be moved from the first position $P_1$ to the second position $P_2$. As a result of the posts 120, 130, the support 138, and the flap 106, the medical article 60 is inhibited from movement in the lateral, longitudinal and vertical directions (e.g., relative to the bracket 102) when coupled to the system 100 as shown in FIG. 3. In some embodiments, moving a portion of the medical article into the first and the second channel occurs substantially simultaneously.

In some preferred embodiments, after placement in the securement system 100, the medical article 60 tilts toward the distal end of the bracket base at an angle τ of 5° to 30°, 8° to 25°, 10° to 20°, or 14° to 15° (e.g., 14.5°) relative to a plane defined by the second major surface of the base. The tilt of the medical article, as described above, can facilitate insertion of a portion of the medical article 60 into a patient and secures the medical article 60 in an orientation that makes it less likely that damage to the patient's blood vessel will occur.

The following embodiments are intended to be illustrative of the present disclosure and not limiting.

SELECT EMBODIMENTS OF THE PRESENT DISCLOSURE

1. A bracket configured for use with a medical article, the bracket comprising:
   a base having a longitudinal axis, a first major surface, a second major surface opposite the first major surface, a distal end, and a proximal end;
   a first set of posts spaced a first lateral distance apart, coupled to the first major surface of the base and extending upwardly from the base in a direction generally normal to the first major surface of the base, the first set of posts defining a first channel dimensioned to receive at least a portion of the medical article and configured to inhibit at least lateral movement of the medical article when the medical article is coupled to the bracket;
   a second set of posts spaced a second lateral distance apart, coupled to the base and positioned a longitudinal distance and proximal to the first set of posts and extending upwardly from the base in a direction generally normal to the first major surface of the base, the second set of posts defining a second channel dimensioned to receive at least a portion of the medical article and configured to inhibit at least lateral movement of the medical article when the medical article is coupled to the bracket; and
   a support positioned in the second channel,
   wherein the first lateral distance is greater than the second lateral distance, and wherein the first set of posts, the second set of posts, and the support are each fixed with respect to the base.

2. The bracket of embodiment 1, wherein the first major surface of the base and the second major surface of the base are generally parallel.

3. The bracket of embodiment 1 or 2, wherein the first major surface of the base and the second major surface of the base form an acute angle less than 30° such that the proximal end of the base is thicker than the distal end of the base.

4. The bracket of any one of embodiments 1-3, wherein at least one of the first set of posts, the second set of posts, and the support is integrally formed with the base.

5. The bracket of any one of embodiments 1-4, wherein at least one of the first set of posts, the second set of posts, and the support is directly coupled to the base.

6. The bracket of any one of embodiments 1-5, wherein the longitudinal distance separating the first set of posts and the second set of posts is 1 mm to 12 mm.

7. The bracket of any one of embodiments 1-6, wherein the first set of posts extends from 7 mm to 11 mm from the first major surface of the base and the second set of posts extends from 5 mm to 10 mm from the first major surface of the base.

8. The bracket of any one of embodiments 1-7, wherein the first channel and the second channel are oriented generally parallel to the longitudinal axis.

9. The bracket of any one of embodiments 1-8, wherein the first channel and the second channel are aligned.

10. The bracket of any one of embodiments 1-9, wherein at least one of the first set of posts and the second set of posts comprises a retaining feature.

11. The bracket of any one of embodiments 1-10, wherein the lateral distance between the posts defining at least one of the first channel and the second channel decreases as the posts extend upwardly from the base, away from the first major surface of the base.

12. The bracket of any one of embodiments 1-11, wherein at least one of the first set of posts and the second set of posts is angled distally from 1° to 30° from a direction generally normal to the first major surface of the base.

13. The bracket of any one of embodiments 1-12, wherein the support is coupled to the base.

14. The bracket of embodiment 13, wherein the support extends from 1 mm to 4 mm from the first major surface of the base.

15. The bracket of any one of embodiments 1-14, wherein the support is coupled to at least one post of the second set of posts.

16. The bracket of any one of embodiments 1-15, wherein the second set of posts are configured to abut an external surface of the medical article to inhibit at least longitudinal movement of the medical article when the medical article is coupled to the bracket.

17. A medical article securement system for securing a medical article, the system comprising:
   a bracket configured to retain at least a portion of the medical article, the bracket comprising:
      a base having a longitudinal axis, a first major surface, a second major surface opposite the first major surface, a distal end, and a proximal end;
      a first set of posts spaced a first lateral distance apart, coupled to the first major surface of the base and extending upwardly from the base in a direction generally normal to the first major surface of the base, the first set of posts defining a first channel dimensioned to receive at least a portion of the medical article and configured to inhibit at least lateral movement of the medical article when the medical article is coupled to the bracket;
      a second set of posts spaced a second lateral distance apart, coupled to the base and positioned a longitudinal distance and proximal to the first set of posts and extending upwardly from the base in a direction generally normal to the first major surface of the base, the second set of posts defining a second channel dimensioned to receive at least a portion of the medical article and configured to inhibit at least lateral movement of the medical article when the medical article is coupled to the bracket; and
      a support positioned in the second channel,
   wherein the first lateral distance is greater than the second lateral distance, and wherein the first set of posts, the second set of posts, and the support are each fixed with respect to the base;
   a base dressing comprising:
      a first side; and
      a second side opposite the first side, the second side comprising a skin-contact adhesive,
   wherein the second major surface of the base is coupled to the first side of the base dressing; and
   a flap comprising:
      a fixed end; and
      a free end that is movable with respect to the bracket between a first position in which the flap is not positioned over the bracket, and a second position in which at least a portion of the flap is positioned over the bracket to further inhibit movement of the medical article relative to the bracket.

18. The medical article securement system of embodiment 17, wherein the first major surface of the base and the second major surface of the base are generally parallel.

19. The medical article securement system of claim 17 or 18, wherein the first major surface of the base and the second major surface of the base form an acute angle less than 30° such that the proximal end of the base is thicker than the distal end of the base.

20. The medical article securement system of any one of embodiments 17-19, wherein at least one of the first set of posts, the second set of posts, and the support is integrally formed with the base.

21. The medical article securement system of any one of embodiments 17-20, wherein at least one of the first set of posts, the second set of posts, and the support is directly coupled to the base.

22. The medical article securement system of any one of embodiments 17-21, wherein the longitudinal distance separating the first set of posts and the second set of posts is 1 mm to 12 mm.

23. The medical article securement system of any one of embodiments 17-22, wherein the first set of posts extends from 7 mm to 11 mm from the first major surface of the base and the second set of posts extends from 5 mm to 10 mm from the first major surface of the base.

24. The medical article securement system of any one of embodiments 17-23, wherein the first channel and the second channel are oriented generally parallel to the longitudinal axis.

25. The medical article securement system of any one of embodiments 17-24, wherein the first channel and the second channel are aligned.

26. The medical article securement system of any one of embodiments 17-25, wherein at least one of the first set of posts and the second set of posts comprises a retaining feature.

27. The medical article securement system of any one of embodiments 17-26, wherein the lateral distance between the posts defining at least one of the first channel and the second channel decreases as the posts extend upwardly from the base, away from the first major surface of the base.

28. The medical article securement system of any one of embodiments 17-27, wherein at least one of the first set of posts and the second set of posts is angled distally from 1° to 30° from a direction generally normal to the first major surface of the base.

29. The medical article securement system of any one of embodiments 17-28, wherein the support is coupled to the base.

30. The medical article securement system of embodiment 29, wherein the support extends from 1 mm to 4 mm from the first major surface of the base.

31. The medical article securement system of any one of embodiments 17-30, wherein the support is coupled to at least one post of the second set of posts.

32. The medical article securement system of any one of embodiments 17-31, wherein the second set of posts is configured to abut an external surface of the medical article to inhibit at least longitudinal movement of the medical article when the medical article is coupled to the bracket.

33. The medical article securement system of any one of embodiments 17-32, wherein the base dressing and the skin-contact adhesive are perforated.

34. The medical article securement system of any one of embodiments 17-33, wherein the base dressing further comprises a release liner.

35. The medical article securement system of any one of embodiments 17-34, wherein the fixed end of the flap is coupled to the bracket.

36. The medical article securement system of any one of embodiments 17-35, wherein the fixed end of the flap is coupled to the base dressing.

37. A method for coupling a medical article to a medical article securement system, the method comprising:
   providing a medical article having an external surface;
   providing a medical article securement system of any of embodiments 17-36;
   moving a first portion of the medical article into the first channel;
   moving a second portion of the medical article into the second channel;
   moving the flap from the first position to the second position.

38. The method of embodiment 37, wherein moving a portion of the medical article into the first and the second channel occurs substantially simultaneously.

39. The method of embodiment 37 or 38, wherein a distal end of the second set of posts is configured to abut the external surface of the medical article.

40. The method of any one of embodiments 37-39, wherein the medical article comprises a Luer-lock style adapter.

41. The method of any one of embodiments 37-40, wherein the medical article tilts toward the distal end of the bracket base at an angle τ of 5° to 30° relative to a plane defined by the second major surface of the base.

42. The method of embodiment 41, wherein angle τ is 8° to 25°, 10° to 20°, or 14° to 15°.

All cited references, patents, and patent applications in the above application for letters patent are herein incorporated by reference in their entirety in a consistent manner. In the event of inconsistencies or contradictions between portions of the incorporated references and this application, the information in the preceding description shall control. The preceding description, given in order to enable one of ordinary skill in the art to practice the claimed disclosure, is not to be construed as limiting the scope of the disclosure, which is defined by the claims and all equivalents thereto.

What is claimed is:

1. A medical article securement system for securing a medical article, the system comprising:
   a bracket configured to retain at least a portion of the medical article, the bracket comprising:
      a base having a longitudinal axis, a first major surface, a second major surface opposite the first major surface, a distal end, and a proximal end;
      a first set of posts spaced a first lateral distance apart, the first set of posts coupled to the first major surface of the base and extending upwardly from the base in a direction generally normal to the first major surface of the base, the first set of posts defining a first channel dimensioned to receive at least a portion of the medical article and configured to inhibit at least lateral movement of the medical article when the medical article is coupled to the bracket;
      a second set of posts spaced a second lateral distance apart, the second set of posts coupled to the base and positioned a longitudinal distance and proximal to the first set of posts and extending upwardly from the base in a direction generally normal to the first major surface of the base, the second set of posts defining a second channel dimensioned to receive at least a portion of the medical article and configured to inhibit at least lateral movement of the medical article when the medical article is coupled to the bracket; and a support positioned in the second channel, wherein the first lateral distance is greater than the second lateral distance, and wherein the first set of posts, the second set of posts, and the support are each fixed with respect to the base;

a base dressing comprising:
   a first side; and
   a second side opposite the first side, the second side comprising a skin-contact adhesive, wherein the second major surface of the base is coupled to the first side of the base dressing; and a flap comprising:
   a fixed end; and
   a free end that is movable with respect to the bracket between a first position in which the flap is not positioned over the bracket, and a second position in which at least a portion of the flap is positioned over the bracket to further inhibit movement of the medical article relative to the bracket wherein the first major surface of the base and the second major surface of the base continuously form an acute angle less than 30° between the proximal end and the distal end such that the proximal end of the base is thicker than the distal end of the base.

2. The medical article securement system of claim 1, wherein at least one of the first set of posts, the second set of posts, and the support is integrally formed with the base.

3. The medical article securement system of claim 1, wherein at least one of the first set of posts, the second set of posts, and the support is directly coupled to the base.

4. The medical article securement system of claim 1, wherein the longitudinal distance separating the first set of posts and the second set of posts is 1 mm to 12 mm.

5. The medical article securement system of claim 1, wherein the first set of posts extends from 7 mm to 11 mm from the first major surface of the base and the second set of posts extends from 5 mm to 10 mm from the first major surface of the base.

6. The medical article securement system of claim 1, wherein the first channel and the second channel are oriented generally parallel to the longitudinal axis.

7. The medical article securement system of claim 1, wherein the first channel and the second channel are aligned.

8. The medical article securement system of claim 1, wherein at least one of the first set of posts and the second set of posts comprises a retaining feature.

9. The medical article securement system of claim 1, wherein a lateral distance between at least one of the first set of posts and the second set of posts defining at least one of the first channel and the second channel decreases as at least one of the first set of posts and the second set of posts extend upwardly from the base, away from the first major surface of the base.

10. The medical article securement system of claim 1, wherein at least one of the first set of posts and the second set of posts is angled distally from 1° to 30° from a direction normal to the first major surface of the base.

11. The medical article securement system of claim 1, wherein the support is coupled to the base.

12. The medical article securement system of claim 11, wherein the support extends from 1 mm to 4 mm from the first major surface of the base.

13. The medical article securement system of claim 1, wherein the support is coupled to at least one post of the second set of posts.

14. The medical article securement system of claim 1, wherein the second set of posts is configured to abut an external surface of the medical article to inhibit at least longitudinal movement of the medical article when the medical article is coupled to the bracket.

15. The medical article securement system of claim 1, wherein the base dressing and the skin-contact adhesive are perforated.

16. The medical article securement system of claim 1, wherein the base dressing further comprises a release liner.

17. The medical article securement system of claim 1, wherein the fixed end of the flap is coupled to the bracket.

18. The medical article securement system of claim 1, wherein the fixed end of the flap is coupled to the base dressing.

19. A method for coupling a medical article to a medical article securement system, the method comprising:
   providing a medical article having an external surface;
   providing a medical article securement system of claim 1;
   moving a first portion of the medical article into the first channel;
   moving a second portion of the medical article into the second channel;
   moving the flap from the first position to the second position.

20. The method of claim 19, wherein moving a portion of the medical article into the first and the second channel occurs substantially simultaneously.

21. The method of claim 19, wherein a distal end of the second set of posts is configured to abut the external surface of the medical article.

22. The method of claim 19, wherein the medical article comprises a Luer-lock style adapter.

23. The method of claim 19, wherein the medical article tilts toward the distal end of the base at an angle $\tau$ of 5° to 30° relative to a plane defined by the second major surface of the base.

24. The method of claim 23, wherein angle $\tau$ is 8° to 25°.

* * * * *